United States Patent
Ueoka et al.

(10) Patent No.: US 6,288,287 B2
(45) Date of Patent: Sep. 11, 2001

(54) PROCESS FOR PREPARING GLYCEROL

(75) Inventors: Hideaki Ueoka; Takanobu Katayama, both of Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/770,288

(22) Filed: Jan. 29, 2001

(30) Foreign Application Priority Data

Jan. 28, 2000 (JP) ................................................ 12-20091

(51) Int. Cl.[7] ............................ C07C 27/26; C07C 31/18
(52) U.S. Cl. .......................... 568/869; 568/852; 568/853; 568/854
(58) Field of Search .................................. 568/869, 854, 568/853, 852

(56) References Cited

U.S. PATENT DOCUMENTS 3,427,230 * 2/1969 Graham .................................. 203/75

FOREIGN PATENT DOCUMENTS

| | | |
|---|---|---|
| 55-157525 | 12/1980 | (JP) . |
| 58-126827 | 7/1983 | (JP) . |
| 60-109534 | 6/1985 | (JP) . |
| 61-140532 | 6/1986 | (JP) . |
| 1-135735 | 5/1989 | (JP) . |
| 2-011529 | 1/1990 | (JP) . |

* cited by examiner

*Primary Examiner*—Samuel Barts
*Assistant Examiner*—Elvis O. Price
(74) *Attorney, Agent, or Firm*—Oblon, Spivak, McClelland, Maier & Neustadt, P.C.

(57) ABSTRACT

A process for preparing a glycerol from a crude glycerol comprising a glycerol, a diol and water, comprising feeding the crude glycerol to a preparation apparatus comprising two or more, serially connected flash towers and a distillation tower connected to a final flash tower, wherein a bottom fraction of each flash tower is fed to a subsequent flash tower; and adjusting an internal pressure of each flash tower to from 0.13 to 40 kPa, an internal temperature of each flash tower to 140° C. or less, a water content of the bottom fraction of the final flash tower to 0.1% by weight or less, and a pressure at bottom of the distillation tower to from 0.13 to 0.90 kPa.

5 Claims, 1 Drawing Sheet

PROCESS FOR PREPARING GLYCEROL

BACKGROUND OF THE INVENTION

1. Field of the Invention

The present invention relates to a process for preparing a glycerol from an aqueous crude glycerol solution containing impurities such as diols.

2. Discussion of the Related Art

One process for preparing a glycerol includes a process that goes through a step of transesterification, hydrolysis or saponification of an oil or fat. In a glycerol-containing solution obtained through esterification or others, there usually exist impurities such as an oily component, an alkali component, a soap component, a salt or diols. In the conventional process, a crude glycerol is obtained by either concentrating the glycerol-containing solution after subjecting the solution to filtration, distillation, treatment with active charcoal, ion-exchange treatment or the like; or concentrating the glycerol-containing solution, and thereafter subjecting the concentrate to treatment with active charcoal, ion-exchange treatment or the like.

A greater part of impurities such as an oily component can be removed by treatments such as filtration. However, a part of impurities, particularly diols of which physical properties are similar to those of the glycerol, such as 1,2-propanediol, 1,3-propanediol, 3-methoxy-1,2-propanediol, or 2-methoxy-1,3-propanediol, cannot be sufficiently removed by these treatments. In addition, the step of concentrating the glycerol-containing solution is purposed for separating water of which physical properties are significantly different from those of the glycerol. Therefore, it would be impossible to reduce the content of the diol respectively to 0.1% by weight or lower in the conventional concentrating step.

In order to solve these problems and to prepare a glycerol having high quality, various studies have been made as disclosed, for instance, in Japanese Patent Laid-Open Nos. Sho 55-157525, Sho 60-109534, Sho 61-140532 and Hei 1-135735.

Japanese Patent Laid-Open No. Sho 55-157525 discloses a process for suppressing an odor by adding a metal compound when a glycerol-containing solution is concentrated. In this process, however, a step is required for removing the added metal compound after the concentration. In addition, a high purity for the glycerol cannot be expected.

Japanese Patent Laid-Open No. Sho 60-109534 discloses a process comprising subjecting a glycerol-containing solution to distillation procedures under reduced pressure of 10 to 20 mbar and at a temperature of from 165° to 180° C. to previously remove the salt, thereafter isolating water with higher boiling impurities by a distillation tower, and purifying the obtained glycerol by a treatment with active charcoal. In this process, however, the process is carried out at a temperature as high as from 165° to 180° C. for removal of salts in the presence of impurities such as an oily component and others. Therefore, color and odor of a glycerol are deteriorated, and consequently, the treatment with active charcoal is undesirably required in the final step. Moreover, since the glycerol after concentration has a high viscosity, it would be extremely difficult to carry out the treatment with active charcoal. Furthermore, also in the rectification treatment, the fact that water is contained in the raw material as a non-condensing component in the tower in an amount of up to 10% by weight renders marked difficulty in the design for vacuum equipment for operating under the indicated degree of vacuum (5 to 10 mbar), whereby an uneconomical equipment design has to be made.

Japanese Patent Laid-Open No. Sho 61-140532 discloses a process comprising adding pentanol to a glycerol-containing solution to remove salts, and thereafter subjecting the glycerol-containing solution to flash distillation twice using a distillation tower, to give a purified glycerol. When the process is applied to the preparation of a glycerol derived from natural source, however, treatments are carried out at very high temperatures such that the temperature in each flash tower is 150° and 170° C., respectively, and that the temperature in the distillation tower is 190° C., so that the deterioration in quality of the glycerol would be unavoidable. In addition, this publication does not disclose operating conditions in the distillation tower for removal of impurities.

Japanese Patent Laid-Open No. Hei 1-135735 discloses a process comprising adding a polycarboxylic acid to a crude glycerol, obtained by concentrating an aqueous glycerol solution to a concentration of 80 to 95% by weight, and distilling the mixed solution. According to this process, a purified glycerol having excellent stabilities in color and odor is prepared. In the process, however, since conditions for the distillation in the process are reduced pressure of from 10 to 20 mmHg and a temperature of from 150° to 170° C., there is a possibility of insufficient degree of vacuum or insufficient temperature for the removal of impurities by distillation. In addition, a treatment with active charcoal may be necessitated in a subsequent step, depending upon the amount of the polycarboxylic acid.

Furthermore, there arise important problems that a method of reuse of water generated in the course of concentration and a treatment method of water as wastewater needs to be studied, and that the yield of a glycerol needs to be improved, from the viewpoint of reduction in costs in the overall process for preparation.

An object of the present invention is to provide a process for preparing a glycerol from a crude glycerol comprising a diol and water, wherein the color and odor can be improved to an extent that post-treatments such as treatment with active charcoal or ion-exchange treatment is unnecessary after the distillation procedure, and individual impurities which are contained in the prepared glycerol can be remarkably reduced.

Another object of the present invention is to provide a process for preparing a glycerol wherein the recovered water is highly purified to an extent that an additional purification process is unnecessary, in a case where the recovered water is reused or treated as a wastewater in the process for preparing a glycerol.

A still another object of the present invention is to provide a process for preparing a glycerol wherein the glycerol-loss amount in the process for preparing a glycerol is reduced.

These and other objects of the present invention will be apparent from the following description.

SUMMARY OF THE INVENTION

According to the present invention, there is provided a process for preparing a glycerol from a crude glycerol comprising a glycerol, a diol and water, comprising the steps of:

feeding the crude glycerol to a preparation apparatus comprising two or more, serially connected flash towers and a distillation tower connected to a final flash tower, wherein a bottom fraction of each flash tower is fed to a subsequent flash tower; and adjusting an internal pressure of each flash tower to from 0.13 to 40 kPa, an internal temperature of each flash tower to 140° C. or less, a water content of the bottom fraction of the final flash tower to 0.1% by weight or less, and a pressure at bottom of the distillation tower to from 0.13 to 0.90 kPa.

DETAILED DESCRIPTION OF THE INVENTION

Figure 1:
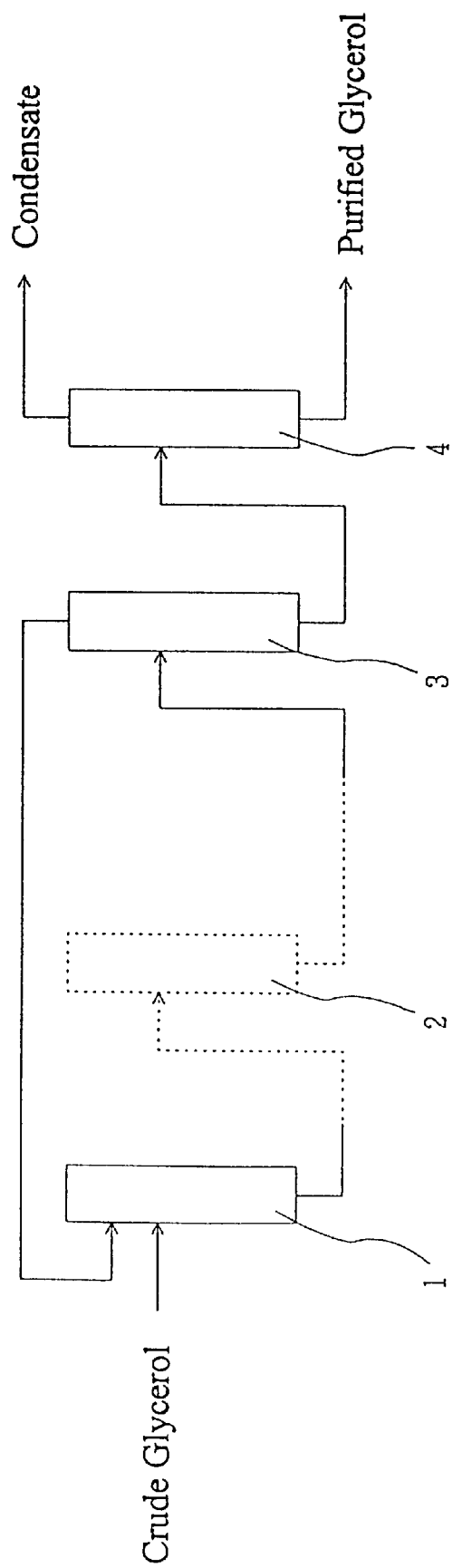
FIG. 1 is a schematic flow chart showing the process of the present invention, wherein 1 is a flash tower to which a crude glycerol is supplied (first flash tower), 2 a flash tower, 3 a final flash tower, and 4 a distillation tower.

The crude glycerol used in the present invention comprises a glycerol, a diol and water. The crude glycerol can be obtained by, for instance, removing an oily component, an alkali component, a soap component and a salt component from an aqueous glycerol solution containing various by-products. The same can be obtained by transesterification, hydrolysis or saponification of a fat or oil. The removal of the oily component and others may be attained by known methods, and an appropriate method may be selected from treatments including, for instance, acid treatment, distillation, filtration, treatment with active charcoal or ion-exchange treatment and used in combination.

The crude glycerol contains, in addition to the glycerol and water, impurities, a great part of which cannot be removed by the above-mentioned method for removing an oily component and others. The impurities include components having structure and physical properties similar to those of the glycerol, specifically diols such as 1,2-propanediol, 1,3-propanediol, 3-methoxy-1,2-propanediol, 2-methoxy-1,3-propanediol and the like.

The contents of the glycerol, water and diols in the crude glycerol are not particularly limited.

In the present invention, before rectification is carried out in a distillation tower, a crude glycerol is firstly fed to two or more flash towers as the raw material, as shown in the flow chart shown in FIG. 1. Each of flash towers is connected in series such that a bottom fraction in one flash tower is fed to another flash tower.

The purpose of the flash distillation is to remove water in a material to be distilled such as the crude glycerol. Water distilled away from the flash tower is condensed in a condenser and recovered, and a glycerol in the bottom fraction is fed to a next flash tower. The procedure for removing water by flash distillation is repeated until the water content in the glycerol obtained from a bottom fraction in the flash tower attains to 0.1% by weight or less.

By adjusting the water content in the bottom fraction in the flash tower to 0.1% by weight or less, preferably 0.08% by weight or less, more preferably 0.05% by weight or less, an entire preparation apparatus can be miniaturized. This is because the inside of the distillation tower is high vacuum, so that the amount of uncondensed and unrecoverable water in the distillation step is reduced, whereby the load for a distillation tower and an annexed vacuum apparatus can be reduced. While the distillation procedure itself can be carried out even if the water content in a glycerol to be fed to the distillation tower exceeds the upper limit of this range, such a method is not practical because scaling up of equipment is unavoidable for the reasons given above. The water content in the bottom fraction is quantified by, for instance, a method for determining water (JIS K0068) defined in the method for analyzing quality of an industrial glycerol (JIS K3351).

Conditions for operating other flash towers (1 and 2 shown in FIG. 1) connected upstream of the final flash tower are determined under conditions such that the water content in the condensate of distillate obtained from the flash tower is preferably 98% by weight or more, more preferably 99% by weight or more. It is preferable to employ the above conditions, because a further purification step becomes unnecessary for the recovery and reuse of the condensate of the distillate, a further treatment step becomes also unnecessary for discarding the condensate of the distillate, and in addition, the yield of a glycerol can be improved. The content of water in the condensate of the distillate refers to a value obtained by subtracting, from the total, the amount of the glycerol and that of impurities (diols) in the condensate as quantified by GC (gas chromatography).

In order to satisfy these conditions, conditions for operating the flash tower can be appropriately selected, for instance, a pressure in the tower within a range of from 0.13 to 40 kPa. The pressure is preferably 0.13 kPa or more, from the viewpoints of condensation of evaporated water and design of vacuum apparatus, and the pressure is preferably 40 kPa or less, from the viewpoint of sufficient separation of water.

In order to efficiently remove water in two or more flash towers connected in series, it is preferable to reduce the pressure in towers in the order of increasing numbers starting from the first tower. Specifically, it is more preferable that the pressure in the flash towers other than the final flash tower is from 2.7 to 40 kPa, especially preferably from 6.5 to 27 kPa. This is because water distilled away from the flash towers can be easily condensed and recovered. Moreover, it is more preferable that the pressure in the final flash tower is from 0.13 to 1.3 kPa, especially preferably from 0.26 to 0.70 kPa.

The temperature in the flash towers is determined depending upon the pressure in the tower. It is preferable that the temperature is 140° C. or less, more preferably from 70° to 140° C., and most preferably from 90° to 130° C., from the viewpoint of suppressing deterioration in odor and color of the obtained glycerol.

The flash tower which can be used in the present invention is not particularly limited. The flash tower includes evaporators of horizontal multi-tube type or basket type having a heater in the inside of a evaporator, and forced circulation type, climbing thin-film type or falling liquid film type having a heating device in the outside of the evaporator. Among them, the evaporators of climbing thin-film type and falling liquid film type are preferred, from the viewpoint of minimizing heat history of the glycerol.

In addition, it is preferred that the condensate of the distillate is fed to a feed of a flash tower for feeding the crude glycerol as shown in FIG. 1 from the final flash tower, i.e., a flash tower immediately before the distillation tower (see 3 in FIG. 1). This is because the glycerol contained in the condensate is recovered and reused for improving the overall yield. While the condensate may be fed to a feed of a distillation tower, from the viewpoint of recovery and reuse of the glycerol, this procedure is not preferred because of increase in the amount of water in the feed of a distillation tower owing to water contained in the condensate.

As shown in FIG. 1, the bottom fraction of the flash tower of which water content attains to 0.1% by weight or less, obtained through two or more flash towers connected in series, is then fed to a distillation tower (4 in FIG. 1). The distillation tower and the flash tower are connected such that the bottom fraction of the final flash tower is fed to the distillation tower. Preferred conditions for operating the distillation tower are those in which a purified glycerol having high purity is obtained, for instance, a glycerol having the total amount of impurities of preferably 1% by weight or less, more preferably 0.5% by weight or less, and an amount of individual impurities of preferably 0.1% by weight or less, more preferably 0.08% by weight or less, is attained.

More preferable conditions for operating the distillation tower are a pressure at bottom of the tower of from 0.13 to 0.90 kPa, preferably from 0.26 to 0.73 kPa, and more preferably from 0.26 to 0.53 kPa. These conditions for operation are determined according to the purpose of decreasing the heat history of the glycerol. In other words, from the viewpoint of preventing deterioration of odor and color of the glycerol, a temperature at bottom of the tower is preferably 160° C. or less, and therefore, the pressure at bottom of the tower is preferably 0.90 kPa or less from the viewpoint of the vapor pressure property of the glycerol. In addition, when the design conditions of the vacuum apparatus as well as pressure drop and diameter of the tower are considered, the pressure at bottom of the tower is preferably 0.13 kPa or more.

More preferably, the pressure at top of the tower is from 0.13 to 0.40 kPa and pressure drop between the top and the bottom of the tower is from 0.13 to 0.80 kPa. The pressure at top of the tower is preferably as low as possible because of the existing pressure drop towards the bottom of the tower, and the pressure is preferably 0.13 kPa or more, from the viewpoint of avoidance of scaling up of equipment. In addition, in order to avoid elevation of the temperature at bottom of the tower, the pressure is preferably 0.40 kPa or less, from the viewpoint of pressure drop. Moreover, the pressure drop in the tower is preferably 0.13 kPa or more from the viewpoint of avoidance of scaling up of equipments. Furthermore, the pressure drop in the tower is preferably 0.80 kPa or less, from the viewpoint of avoidance of elevation of the temperature at bottom of the tower. The pressure at top of the tower is preferably from 0.13 to 0.33 kPa and more preferably from 0.13 to 0.27 kPa. The above-mentioned pressure drop is preferably from 0.13 to 0.53 kPa and more preferably from 0.20 to 0.40 kPa.

In addition, the number of stages in the distillation tower is preferably 4 or more, more preferably 6 to 10 and most preferably 6 to 8, excluding a reboiler and a condenser. When the number of stages is too small, a larger reflux ratio becomes necessary for satisfying the desired purity of the glycerol, and consequently, making it not only economically disadvantageous but also poor in qualities such as odor and color due to increase in heat history of the glycerol. Therefore, the number of stages in the distillation tower is preferably 4 or more. From the viewpoint of manufacturing costs of equipments, the number of stages is preferably 10 or less.

The number of stages in the distillation tower herein refers to a value obtained by dividing the theoretical number of stages by tower efficiency, and the theoretical number of stages refers to a number in which compositions of vapor and liquid leaving the stage are at equilibrium.

The distillation tower which can be used in the present invention is possibly a stage tower type having a tray such as bubble cap tray, perforated tray or bubble plate tray in the tower, packed tower type filled with random packing such as Raschig ring or the like, or packed tower type filled with structured packing such as Sulzer packing or the like. Among them, structured packing is preferred from the viewpoints of pressure drop and heat history.

The position of feed in the distillation tower is not particularly limited. It is preferably positioned in a top part of the tower from the viewpoint of simplification of the structure of the tower.

The condenser at top of the distillation tower is preferably a partial condenser because of a high degree of vacuum at top of the tower. It is preferable that it takes the form of discharging only vapor that is not condensed in the condenser as a distillate and returning the entire condensate into the tower as a reflux. In addition, it is preferable that the condenser is of the intra-tower installing type, and that its pressure drop is as low as possible. More preferably, the cooling temperature in the condenser is from 80° to 130° C., and the condensate is refluxed without being supercooled.

The vapor that is not condensed in the condenser at the top part of the tower is condensed in a subsequent after-condenser. Impurities other than water, particularly diols, are concentrated in the condensate. In order to improve the yield of the glycerol, the temperature at top of the distillation tower and the amount of the distillate are determined such that the content of the glycerol in the condensate is preferably 1% by weight or less, more preferably 0.5% by weight or less.

EXAMPLES

Example 1

A glycerol-containing solution obtained through transesterification reaction of natural fats and oils was subjected to known acid treatment, filtration, addition of water, oil separation, active charcoal treatment and ion-exchange treatment by known methods, to give a crude glycerol. The composition is shown in Table 1. As to the determination of the composition, each of glycerol and the diols was quantified by GC, and the water content was determined by Karl-Fischer titration method (in accordance with JIS K0068).

TABLE 1

|  | Example 1 | Example 4 | Example 7 |
| --- | --- | --- | --- |
| Glycerol | 51.4 | 80.8 | 49.3 |
| Water | 47.3 | 16.8 | 49.3 |
| 3M-PD | 1.0 | 1.9 | 0 |
| 2M-PD | 0.3 | 0.5 | 0 |
| 1,2-PD | 0 | 0 | 1.0 |
| 1,3-PD | 0 | 0 | 0.4 |

In Table 1, 3M-PD stands for 3-methoxy-1,2-propanediol, 2M-PD stands for 2-methoxy-1,3-propanediol, 1,2-PD stands for 1,2-propanediol, and 1,3-PD stands for 1,3-propanediol, respectively.

A glycerol was prepared by feeding each of the crude glycerol to a preparation apparatus comprising 3 serially connected flash towers and a distillation tower connected to a final tower. Here, each of the towers was connected so that a bottom fraction of each tower is fed to a subsequent tower. The operation conditions for each tower and the quality of the resulting glycerol are shown in Tables 2 and 3.

The quantification of the diol in the resulting glycerol was carried out by GC (commercially available from Supelco, OVI-G43 column). The color (APHA) of the resulting glycerol was determined by the determination method for color as defined in JIS K3351. The reflux ratio is a value obtained by dividing an amount of liquid obtained from condensing the crude glycerol in the condenser at top of the tower and returning into the tower (reflux flow rate) by an amount of steam distilled away at top of the tower. In addition, the term "glycerol-loss" refers to a proportion of the glycerol lost in the present glycerol preparation apparatus, and is obtained by dividing a glycerol flow rate contained in the steam distilled away from the distillation tower by a glycerol flow rate contained in the crude glycerol.

In addition, each of the first flash tower and the second flash tower was a climbing thin-film type. The final flash tower was a falling liquid film type. The distillation tower was a packed tower using fillers with regularities.

connected flash towers and a distillation tower connected to a final tower. Here, each of the towers was connected so that a bottom fraction of each tower is fed to a subsequent tower. The operation conditions for each tower and the quality of the resulting glycerol are shown in Tables 2 and 3.

Examples 5 and 6

A glycerol was prepared in the same manner as in Example 3, except for changing the internal pressure and the number of stages for the distillation tower.

Example 7

A glycerol-containing solution obtained through hydrolysis reaction of natural fats and oils was subjected to oil separation, active charcoal treatment and ion-exchange treatment by known methods, to give a crude glycerol. The composition is shown in Table 1.

TABLE 2

| | First Flash Tower | | Second Flash Tower | | Final Flash Tower | | Distillation Tower | | | |
|---|---|---|---|---|---|---|---|---|---|---|
| Example No. | Pressure [kPa] | Temp [° C.] | Pressure [kPa] | Temp. [° C.] | Pressure [kPa] | Temp. [° C.] | Number of Stages | Pressure at Top [kPa] | Pressure at Bottom [kPa] | Temp. at Bottom [° C.] |
| 1 | 26 | 90 | 11.7 | 90 | 0.52 | 120 | 6 | 0.13 | 0.33 | 139.6 |
| 2 | 26 | 90 | 11.7 | 90 | 0.52 | 120 | 4 | 0.13 | 0.33 | 139.6 |
| 3 | 26 | 90 | 11.7 | 90 | 0.52 | 120 | 2 | 0.13 | 0.33 | 139.5 |
| 4 | 11.7 | 90 | 0.52 | 130 | — | — | 4 | 0.13 | 0.33 | 139.5 |
| 5 | 11.7 | 90 | 0.52 | 130 | — | — | 4 | 0.13 | 0.52 | 148.5 |
| 6 | 11.7 | 90 | 0.52 | 130 | — | — | 6 | 0.39 | 0.78 | 156.6 |
| 7 | 26 | 90 | 18.9 | 90 | 0.65 | 120 | 4 | 0.13 | 0.33 | 139.5 |

Examples 2 and 3

A glycerol was prepared in the same manner as in Example 1, except for changing the number of stages for the distillation tower.

Example 4

A glycerol-containing solution obtained through transesterification reaction of natural fats and oils was subjected to acid treatment, filtration, oil separation, active charcoal treatment and ion-exchange treatment by known methods, to give a crude glycerol. The composition is shown in Table 1.

A glycerol was prepared by feeding each of the crude glycerol to a preparation apparatus comprising 2 serially connected flash towers and a distillation tower connected to a final tower. Here, each of the towers was connected so that a bottom fraction of each tower is fed to a subsequent tower. The operation conditions for each tower and the quality of the resulting glycerol are shown in Tables 2 and 3.

A glycerol was prepared by feeding each of the crude glycerol to a preparation apparatus comprising 3 serially connected flash towers and a distillation tower connected to a final tower. Here, each of the towers was connected so that a bottom fraction of each tower is fed to a subsequent tower. The operation conditions for each tower and the quality of the resulting glycerol are shown in Tables 2 and 3.

TABLE 3

| | First Flash Tower | | Second Flash Tower | | Final Flash Tower | Distillation Tower | | | | | Glycerol- |
|---|---|---|---|---|---|---|---|---|---|---|---|
| Example No. | Water Content of Distillate [wt %] | Water Content of Bottom [wt %] | Water Content of Distillate [wt %] | Water Content of Bottom [wt %] | Water Content of Bottom [wt %] | 3M-PD* [wt %] | 2M-PD* [wt %] | Odor | Color APHA | Reflux Ratio | Loss [%] |
| 1 | 99.7 | 10.7 | 99.1 | 3.9 | 0.04 | 0.06 | 0.08 | None | 5> | 6.0 | 0.25 |
| 2 | 99.7 | 10.7 | 99.1 | 3.9 | 0.04 | 0.08 | 0.07 | None | 5> | 8.1 | 0.26 |
| 3 | 99.7 | 10.7 | 99.1 | 3.9 | 0.04 | 0.09 | 0.07 | None | 5> | 20.0 | 0.27 |
| 4 | 99.1 | 3.9 | — | — | 0.02 | 0.09 | 0.08 | None | 5> | 9.4 | 0.38 |
| 5 | 99.1 | 3.9 | — | — | 0.02 | 0.09 | 0.08 | None | 5> | 9.4 | 0.38 |
| 6 | 99.1 | 3.9 | — | — | 0.02 | 0.08 | 0.08 | None | 5> | 6.9 | 0.37 |
| 7 | 99.4 | 10.7 | 99.1 | 6.9 | 0.05 | 0 | 0.07 | None | 5> | 5.9 | 0.08 |

Note
*In Example 7, 1,2-PD and 1,3-PD were used instead of 3M-PD and 2M-PD, respectively.

As described above, according to the process of the present invention, a glycerol having little impurity content and excellent in odor and color can be obtained. Any of these resulting glycerols have such a high purity that a further treatment is unnecessary.

Comparative Example 1

A glycerol was prepared in the same manner as in Example 1 except for the operating conditions for the flash distillation. The operating conditions for each tower and the quality of the resulting glycerol are shown in Table 4.

When the internal temperature of the flash tower is higher, the quality of the resulting glycerol is poor and the odor is deteriorated even when other operating conditions are set within the scope of the present invention.

Comparative Example 2

A glycerol was prepared in the same manner as in Example 4 except for the internal pressure of the distillation tower. The operating conditions for each tower and the quality of the resulting glycerol are shown in Table 4.

By adjusting a pressure at bottom of the distillation tower to that exceeding 0.90 kPa and an internal temperature of the distillation tower to 160° C. or more, both odor and color of the resulting glycerol were deteriorated.

variations are not to be regarded as a departure from the spirit and scope of the invention, and all such modifications as would be obvious to one skilled in the art are intended to be included within the scope of the following claims.

What is claimed is:

1. A process for recovering glycerol from a crude glycerol comprising glycerol, a diol and water, comprising the steps of:

feeding the crude glycerol to a preparation apparatus comprising two or more, serially connected flash towers and a distillation tower connected to a final flash tower, wherein a bottom fraction of each flash tower is fed to a subsequent flash tower; and adjusting an internal pressure of each flash tower to 0.13 to 40 kPa, an internal temperature of each flash tower to 140° C. or less, a water content of the bottom fraction of the final flash tower to 0.1% by weight or less, and a pressure at the bottom of the distillation tower to 0.13 to 0.90 kPa.

2. The process according to claim 1, wherein flash distillation is carried out such that the water content of a condensate of a fraction obtained from another flash tower connected to upstream of the final flash tower is 98% by weight or more.

TABLE 4

| | First Flash Tower | | Second Flash Tower | | Final Flash Tower | | Distillation Tower | | | |
|---|---|---|---|---|---|---|---|---|---|---|
| Comp. Ex. No. | Pressure [kPa] | Temp. [° C.] | Pressure [kPa] | Temp. [° C.] | Pressure [kPa] | Temp. [° C.] | Number of Stages | Pressure at Top [kPa] | Pressure at Bottom [kPa] | Temp. at Bottom [° C.] |
| 1 | 26 | 90 | 11.7 | 90 | 1.04 | 145 | 6 | 0.13 | 0.52 | 148.5 |
| 2 | 11.7 | 90 | — | — | 0.52 | 130 | 4 | 0.65 | 1.43 | 170.3 |

| | First Flash Tower | | Second Flash Tower | | Final Flash Tower | | | | | |
|---|---|---|---|---|---|---|---|---|---|---|
| | Water Content of | Water Content of | Water Content of | Water Content of | Water Content of | Distillation Tower | | | | Glycerol- |
| Comp. Ex. No. | Distillate [wt %] | Bottom [wt %] | Distillate [wt %] | Bottom [wt %] | Bottom [wt %] | 3M-PD [wt %] | 2M-PD [wt %] | Odor | Color APHA | Reflux Ratio | Loss [%] |
| 1 | 99.7 | 10.7 | 99.1 | 3.9 | 0.03 | 0.05 | 0.07 | Slightly burnt odor | 5 | 12.0 | 0.34 |
| 2 | 99.1 | 3.9 | — | — | 0.02 | 0.09 | 0.07 | Burnt odor | 15 | 11.2 | 0.27 |

According to the process of the present invention, there can be obtained a purified glycerol having a remarkably reduced impurity content and being excellent in color and odor. Also, the water discharged from the above steps has excellent purity such that a further purification step is unnecessary, whereby the collection and reuse or waste disposal can be facilitated. Further, the yield of the glycerol can be improved.
Equivalent The present invention being thus described, it will be obvious that the same may be varied in many ways. Such 3. The process according to claim 1, wherein a condensate of a fraction from the final flash tower is fed to the feed of a flash tower to which said crude glycerol is fed.

4. The process according to claim 1, wherein a pressure at top of the distillation tower is from 0.13 to 0.40 kPa, and a pressure drop between top and bottom of the distillation tower is from 0.13 to 0.80 kPa.

5. The process according to claim 1, wherein the number of steps of the distillation tower is 4 or more.

* * * * *